(12) United States Patent
Riondel et al.

(10) Patent No.: US 6,841,697 B2
(45) Date of Patent: Jan. 11, 2005

(54) PROCESS FOR PREPARING 2-(DIMETHYLAMINO)-1-(DIMETHYL-AMINOMETHYL) ETHYL METH (ACRYLATE)

(75) Inventors: Alain Riondel, Forbach (FR); Fabrice Castellani, Saint-Avold (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 10/132,739

(22) Filed: Apr. 26, 2002

(65) Prior Publication Data

US 2002/0183543 A1 Dec. 5, 2002

(30) Foreign Application Priority Data

Apr. 26, 2001 (FR) .............................. 01 05609

(51) Int. Cl.$^7$ ................... C07C 67/02; C07C 67/03; C07C 69/52
(52) U.S. Cl. ...................... 560/217; 560/222
(58) Field of Search .................. 560/217, 222

(56) References Cited

U.S. PATENT DOCUMENTS

| 3,784,566 A | * | 1/1974 | Patterson | .................... 260/486 |
| 5,912,383 A | | 6/1999 | Riondel et al. | |

FOREIGN PATENT DOCUMENTS

| DE | 3048 020 A1 | 7/1982 |
| EP | 0 250 325 A2 | 12/1987 |
| EP | 0281 718 A2 | 9/1988 |
| EP | 0 329 512 A | 8/1989 |
| EP | 0420790 A1 | 4/1991 |
| EP | 0 428 970 A | 5/1991 |
| EP | 0663386 A1 | 7/1995 |
| EP | 0930 290 A1 | 7/1999 |
| FR | 1 529 000 A | 10/1968 |
| FR | 2 027 225 | 9/1970 |
| FR | 2 707 291 | 1/1995 |
| FR | 2 788 767 | 7/2000 |
| JP | 11246495 | * 9/1999 |
| WO | WO 89/07588 | 8/1989 |

OTHER PUBLICATIONS

Solovskii et al, "Synthesis and antimicrobial properties of mono– and polymeric quatemary ammonium salts containing aminoalkyl esters of methacrylic acid" Khimiko–Farmatsevticheskii Zhurnal, vol. 8(6), pp. 20–24 (1974). As Abstracted by CAPLUS.*
Korshunov et al, Zhurnal Organicheskoi Khimii, vol. 5(11), pp. 1947–1952, (1960), (Translation).*
Solovskii et al, "Synthesis and antimicrobial properties of mono– and polymeric quaternary ammonium salts containing aminoalkyl esters of methacrylic acid" Khimiko–Farmatsevticheskii Zhurnal, vol. 8(6), pp. 20–24 (1974). Translation.*
Abstract of JP 07 238057 A, Sep. 12, 1995.
Abstract of JP 10 072433 A, Mar. 17, 1998.

* cited by examiner

*Primary Examiner*—Richard L. Raymond
*Assistant Examiner*—Zachary C. Tucker
(74) *Attorney, Agent, or Firm*—Millen White Zelano & Branigan, P.C.

(57) ABSTRACT

Process for preparing a compound (I) by reacting a compound of formula (II) with the alcohol (III).

The reaction is carried out using dibutyltin oxide as transesterification catalyst.

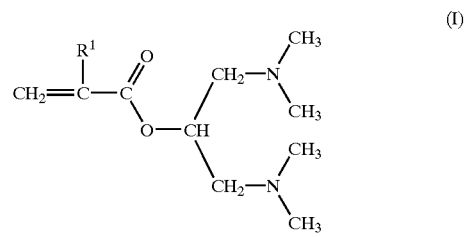

(I)

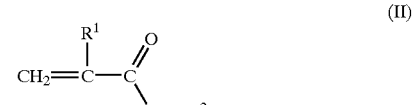

(II)

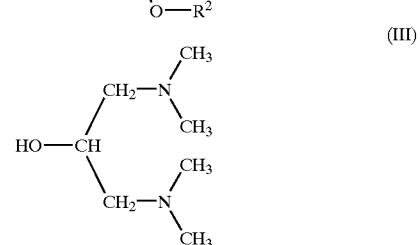

(III)

$R^1$=H or $CH_3$
$R^2$=linear $C_1$–$C_4$ alkyl radical.

15 Claims, No Drawings

PROCESS FOR PREPARING 2-(DIMETHYLAMINO)-1-(DIMETHYL-AMINOMETHYL) ETHYL METH (ACRYLATE)

CROSS-REFERENCE TO RELATED APPLICATIONS

The present application is related to U.S. application Ser. No. 10/132,691, filed Apr. 26, 2002 based on French priority application No. 01.05610, filed Apr. 26, 2001, and U.S. application Ser. No. 10/132,690, filed Apr. 26, 2002 based on French priority application No. 01.05701, filed Apr. 27, 2001.

The present invention relates to a process for preparing compounds of formula (I):

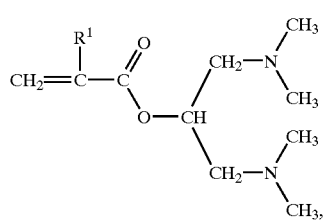

in which $R^1$ represents hydrogen or a methyl group, which are also referred to hereinbelow by the abbreviations S-ADAME (for 2-(dimethylamino)-1-(dimethylaminomethyl)ethyl acrylate) and S-MADAME (for 2-(dimethylamino)-1-(dimethylaminomethyl)ethyl methacrylate).

S-ADAME and S-MADAME may be quaternized on one or both nitrogens to give the following compounds respectively using, for example, benzyl chloride as quaternizing agent:

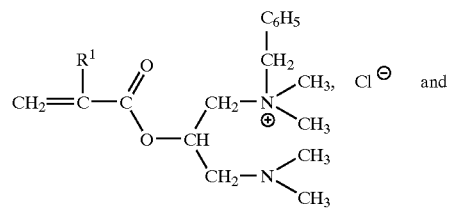

(S-(M) ADAMQUAT BZ)

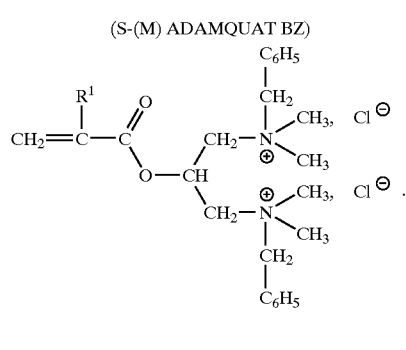

(S-(M)-ADAMQUAT 2BZ)

The aqueous solutions of quaternary salts obtained in this way are used in particular for preparing polymers intended for use as cationic flocculants in water treatment.

S(M)-ADAME is prepared by reacting 1,3-bisdimethylamino-2-propanol:

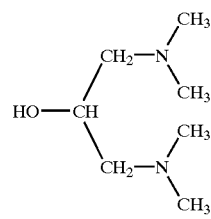

with (meth)acrylic anhydride in the presence of triethylamine with a (meth)acrylic anhydride/1,3-bisdimethylamino-2-propanol molar ratio of from 0.5 to 2, at a temperature from 20 to 100° C., in particular from 30 to 60° C., for a duration of from 2 to 10 hours, in the presence of at least one stabilizer, such as phenothiazine, hydroquinone methyl ether, 3,5-di-tert-butyl-4-hydroxytoluene and hydroquinone and mixtures of these stabilizers in a proportion of from 200 to 3000 ppm relative to the batch. In the reaction with (meth)acrylic anhydride, the triethylamine serves to catalyse the reaction and to scavenge the (meth) acrylic acid formed in salt form. It is generally used in a proportion of from 1 to 2 molar equivalents relative to the (meth)acrylic anhydride.

This process, however, is not easy to practise on the industrial scale on account of the fact that it gives rise to large quantities of salt waste deriving from the scavenging of the acrylic acid by the triethylamine.

Additionally, M. A. Korshonov, F. N. Bondaryuk and V. S. Mikhlin, Zh. Org. Khim. 1969 5(11) 1947–1952, have described the synthesis of S-ADAME by transesterification using tetrabutyl titanate as catalyst. However, the purity of the products obtained by this process is inadequate.

Looking for a process which can be practised industrially for preparing the compounds of formula (I) with a greater purity, it has been discovered that this twin aim was surprisingly achievable by using dibutyltin oxide as catalyst in the preparation of compounds of formula (I) by transesterification.

The present invention accordingly provides a process for preparing a compound of formula (I):

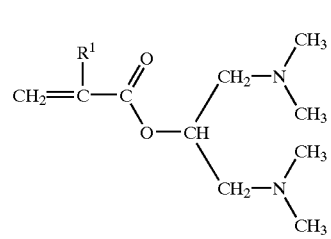

in which $R^1$ represents hydrogen or a methyl radical by reacting a compound of formula (II):

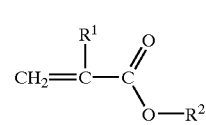

in which $R^2$ represents a linear $C_1$–$C_4$ alkyl radical with the alcohol of formula (III):

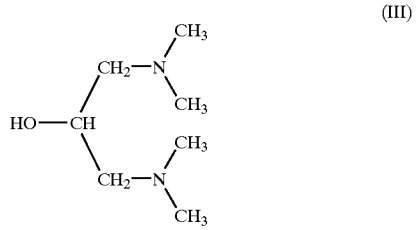

(III)

characterized in that the reaction is carried out using dibutyltin oxide in catalytic quantities as transesterification catalyst.

In accordance with various preferred features of the process of the present invention:

dibutyltin oxide is used in an amount of from 0.5 to 5 mol %, in particular in an amount of from 1 to 3 mol % relative to the alcohol of formula (III);

the reaction is carried out at a temperature from 110 to 180° C., in particular from 140 to 160° C.;

the reaction is carried out with a (meth)acrylate (II)/alcohol (III) molar ratio of from 1.5 to 5, in particular from 2 to 3;

n-butyl (meth)acrylate is used as compound (II);

the reaction is carried out in the presence of from 500 to 3000 ppm with at least one stabilizer relative to the batch, the stabilizer or stabilizers advantageously being selected from phenothiazine, di-tert-butylhydroxytoluene, hydroquinone methyl ether, paraphenylenediamine and mixtures thereof in any proportion.

The examples which follow illustrate the present invention without, however, limiting its scope. In these examples, the parts and percentages indicated are by weight unless stated otherwise and the following abbreviations have been used:

| BUA | n-butyl acrylate |
|---|---|
| DBTO | dibutyltin oxide |
| Zr(acac)$_4$ | zirconium acetylacetonate |
| S-ADAME | 2-(dimethylamino)-1-(dimethylamino-methyl)ethyl acrylate |
| PTZ | phenothiazine |
| BHT | di-tert-butylhydroxytoluene |

EXAMPLE 1

A one litre, jacketed glass reactor equipped with a temperature measuring probe, a dip tube for introducing the air required for stabilization, a variable-speed mechanical stirrer and an adiabatic column of the Vigreux type with a top-mounted reflux attachment is charged with:

154.74 g of 1,3-bisdimethylamino-2-propanol;
496.96 g of BUA and
0.45 g of PTZ and 0.45 g of BHT as stabilizers.

The mixture is brought to boiling under reduced pressure ($1.66 \times 10^4$ Pa–166 mbars) and the water is removed by azeotropic distillation with the acrylate (the water present is that contained in the reactants and, more particularly, in the 1,3-bisdimethylamino-2-propanol). In this step, approximately 100 g of a BUA/H$_2$O mixture containing more than 99% BUA is removed.

Subsequently, 7.91 g of DBTO are introduced into the reactor. The pressure is set at $8.1 \times 10^4$ Pa (810 mbars) and the temperature during the reaction changes from 145 to 159° C. The withdrawal of the BUA/BuOH azeotrope is regulated by means of a setpoint temperature at the head of the column (equal to 117° C.)

The reaction is stopped when formation of butanol is no longer observed at the head of the column; in other words, when the temperature at the head of the column is equal to that at which butyl acrylate boils under $8.1 \times 10^4$ Pa (810 mbars).

S-ADAME is obtained by distilling the crude reaction mixture under reduced pressure. Its purity is 99%.

EXAMPLE 2

(Comparative)

Example 1 is repeated but replacing the DBTO by Zr(acac)$_4$.

The purity of the S-ADAME obtained by distilling the crude reaction mixture under reduced pressure does not exceed 98%.

EXAMPLE 3

(Comparative)

Example 1 is repeated but replacing the DBTO by n-butyl titanate.

The purity of the S-ADAME obtained by distilling the crude reaction mixture under reduced pressure does not exceed 98%.

The preceding examples can be repeated with similar success by substituting the generically or specially described reactants and/or operating conditions of this invention for those used in the preceding examples.

The entire disclosure of all applications, patents and publications, and of corresponding French Application No. 01.05609, filed Apr. 26, 2001, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a catalytic process for preparing a compound of formula (I):

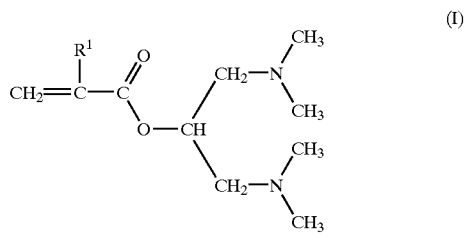

(I)

in which R$^1$ represents hydrogen or a methyl radical comprising reacting a compound of formula (II):

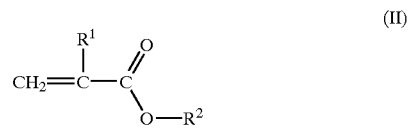

(II)

in which R$^2$ represents a linear C$_1$–C$_4$ alkyl radical with the alcohol of formula (III):

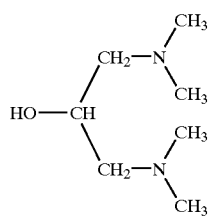

(III)

the improvement wherein the reaction is carried out using dibutyltin oxide in catalytic quantities as a transesterification catalyst.

2. A process according to claim 1, wherein dibutyltin oxide is used in an amount of 0.5–5 mol % relative to the alcohol of formula (III).

3. A process according to claim 1, wherein the dibutyltin oxide is used in an amount of 1–3 mol % relative to the alcohol of formula (III).

4. A process according to claim 1, wherein the reaction is carried out at a temperature of 110–180° C.

5. A process according to claim 1, wherein the reaction is carried out at a temperature of 140–160° C.

6. A process according to claim 1, wherein the reaction is carried out with a (meth)acrylate (II)/alcohol (III) molar ratio of 1.5–5.

7. A process according to claim 1, wherein the reaction is carried out with a (meth)acrylate (II)/alcohol (III) molar ratio of 2–3.

8. A process according to claim 1, wherein the reaction is carried out in the presence of 500–3000 ppm of at least one stabilizer relative to the batch.

9. A process according to claim 1, wherein a stabilizer is phenothiazine, di-tert-butylhydroxytoluene, hydroquinone methyl ether, para-phenylenediamine or a mixture thereof in any proportion.

10. A process according to claim 1, further comprising quaternizing one or both nitrogens to produce a compound of formula:

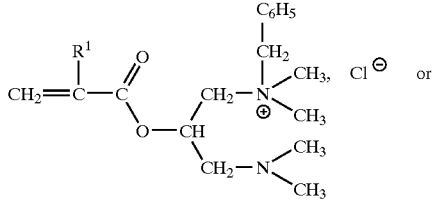

or

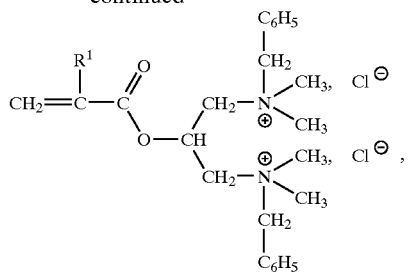

or a mixture thereof in an aqueous solution.

11. A process according to claim 1, further comprising reacting a compound of formula (I) with a quarternizing agent.

12. A process according to claim 10, wherein a quarternizing agent is benzyl chloride.

13. A process according to claim 1, further comprising distilling to obtain a purity of at least 99% of the compound of formula (I).

14. A process according to claim 1, further comprising distilling to obtain a purity of 99% of the compound of formula (I).

15. A catalytic process for preparing a compound of formula (I):

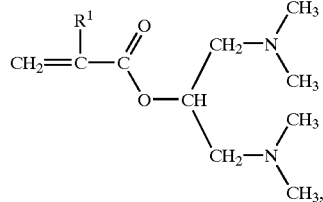

(I)

in which $R^1$ represents hydrogen or a methyl radical comprising reacting n-butyl meth(acrylate) with an alcohol of formula (III):

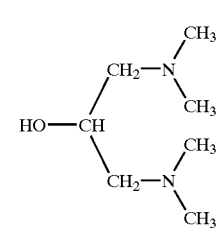

(III)

in the presence of catalytic quantities of dibutyltin oxide as a transesterification catalyst.

* * * * *